(12) United States Patent
Bettenga et al.

(10) Patent No.: US 11,589,860 B2
(45) Date of Patent: Feb. 28, 2023

(54) SYSTEM AND METHOD FOR TRANSPORTING SUTURE

(71) Applicants: Smith & Nephew, Inc., Memphis, TN (US); Smith & Nephew Orthopaedics AG, Zug (CH); Smith & Nephew Asia Pacific Pte Limited, Singapore (SG)

(72) Inventors: Mason Bettenga, Memphis, TN (US); Dirk Wunderle, Zurich (CH); Alexander Iwan Seidl, Zurich (CH); Pascal Boileau, Nice (FR); John Albert Slusarz, Jr., Mansfield, MA (US)

(73) Assignees: Smith & Nephew, Inc., Memphis, TN (US); Smith & Nephew Orthopaedics AG; Smith & Nephew Asia Pacific Pte, Limited, Singapore (SG)

( * ) Notice: Subject to any disclaimer, the term of this patent is extended or adjusted under 35 U.S.C. 154(b) by 195 days.

(21) Appl. No.: 16/937,983

(22) Filed: Jul. 24, 2020

(65) Prior Publication Data
US 2021/0022728 A1 Jan. 28, 2021

Related U.S. Application Data

(60) Provisional application No. 62/878,143, filed on Jul. 24, 2019.

(51) Int. Cl.
| | | |
|---|---|---|
| *A61B 17/04* | (2006.01) | |
| *A61B 17/68* | (2006.01) | |
| *A61B 17/17* | (2006.01) | |
| *A61B 17/84* | (2006.01) | |
| *A61B 17/56* | (2006.01) | |

(52) U.S. Cl.
CPC ...... *A61B 17/0482* (2013.01); *A61B 17/1796* (2013.01); *A61B 17/683* (2013.01); *A61B 17/842* (2013.01); *A61B 2017/564* (2013.01)

(58) Field of Classification Search
CPC ............ A61B 17/0482; A61B 17/0483; A61B 17/1796
See application file for complete search history.

(56) References Cited

U.S. PATENT DOCUMENTS

| | | | | |
|---|---|---|---|---|
| 2,291,413 A | * | 7/1942 | Siebrandt ........... | A61B 17/8861 606/103 |
| 2,577,240 A | * | 12/1951 | Findley ............. | A61B 17/0491 112/169 |
| 5,681,333 A | * | 10/1997 | Burkhart ........... | A61B 17/1778 606/104 |
| 2003/0078600 A1 | * | 4/2003 | O'Quinn ........... | A61B 17/0469 606/144 |

(Continued)

*Primary Examiner* — Christian A Sevilla
(74) *Attorney, Agent, or Firm* — Norman F. Hainer, Jr.

(57) ABSTRACT

A suture transport system is disclosure for placing a flexible member along a tunnel, the system including a means of transporting a flexible member along a tunnel from a first opening in the tunnel through to a second opening at an opposite end of the tunnel, such that the flexible member extends from both the first and second opening. The system also includes a means of capturing a portion of the flexible member at the second opening, to inhibit the flexible member from retracting into the tunnel second opening. The means of capturing includes an aperture for capturing the portion of the flexible member.

12 Claims, 12 Drawing Sheets

(56) References Cited

U.S. PATENT DOCUMENTS

2007/0088362 A1\* 4/2007 Bonutti .................. A61B 17/82
  606/99
2013/0231669 A1\* 9/2013 Sinnott .............. A61B 17/1739
  606/86 R \* cited by examiner

SYSTEM AND METHOD FOR TRANSPORTING SUTURE

CROSS-REFERENCE TO RELATED APPLICATIONS

This application claims priority to U.S. Provisional App. No. 62/878,143 filed Jul. 24, 2019, titled SYSTEM AND METHOD FOR TRANSPORTING SUTURE, herein incorporated by reference in its entirety.

This application also incorporates by reference commonly owned U.S. Pat. No. 9,962,149; herein incorporated by reference in its entirety. This application also incorporates by reference U.S. Pat. No. 9,402,650, commonly owned and herein incorporated in its entirety by reference. This application also incorporates by reference U.S. Pat. No. 9,211,118, commonly owned and herein incorporated in its entirety by reference.

FIELD OF THE INVENTION

The present invention relates to suture transporting techniques, devices and methods, and in particular, to a method and system for transporting a flexible member through a tissue tunnel such as from one side of a bone to another and providing a reliable means of capturing the flexible member thereafter.

BACKGROUND

When passing a length of a flexible member such as tape or suture through tissue and/or bone tunnel, it can often be time consuming and particularly challenging to discover or catch the flexible member at the other end. Oftentimes after drilling a tunnel or making an opening through tissue, a length of a flexible member is subsequently pushed through the tunnel or opening and manually retrieved at the other end. This technique may enable coupling and drawing a secondary element such as a graft or tissue repair construct into this other tunnel end. Retrieving this flexible member however may require an extra skin incision adjacent this tunnel end, to visualize and thereby grasp the flexible member, which can add procedure time to close the incision as well as add unnecessary incision scars visible on the patient's skin. Retrieving this flexible member can be difficult, as the flexible member may be challenging to observe, especially in tightly constrained areas such as a joint of a knee or generally in arthroscopic or endoscopic procedures. Flexible members may easily retract back into the tunnel also. There is therefore a need to more reliably transport, discover and capture a flexible member once through the opening or tunnel. There is also a need to reliably retrieve a flexible member once through the opening or tunnel to subsequently draw a secondary element into the tunnel end with reduced skin incisions.

SUMMARY

Generally this disclosure describes a system for reliably transporting a flexible member through from a first side of tissue to a second side and the retrieving this flexible member. This may include transporting a length of a flexible member such as suture or tape through a prepared tunnel though tissue such as at least one bone. This flexible member may then act as a shuttle and draw a secondary element into the tunnel. Being flexible is preferable, so the flexible member can more readily flex around the bone and out of a patient skin incision that may be laterally spaced from the tunnel end. In addition, this flexible member once attached to a secondary element at a more convenience location may be shutting back around the bone and into the tunnel. Secondary elements may include for example a graft, or an adjustable tissue repair system.

The system described herein may include an AC joint guide system and a deployable all-suture anchor for example. Non-limiting examples of all-suture anchors may include the Q-Fix◊ all-suture implant, generally described in U.S. Pat. No. 9,962,149, commonly owned and incorporated in its entirety by reference herein. Other non-limiting examples of anchors may include the SutureFix◊ all-suture implant, generally described in U.S. Pat. No. 8,795,334, commonly owned and incorporated in its entirety by reference herein. Other non-limiting examples of anchors that are not all-suture anchors may include the toggle implants employed in the FastFix◊ meniscal repair system. Passing elements through tunnels may be required during knee surgery, such as ACL reconstructive surgery, shoulder surgery such as during a Laterjet procedure or Ankle Syndesmosis stabilization for example.

Disclosed herein is a first non-limiting example embodiment of a suture transport system for placing a shuttling flexible member along a tunnel. The system includes a means of transporting a flexible member along a tunnel. The tunnel may extend from a first cortical surface of a bone to a second cortical surface of a bone. The tunnel may extend through two bones adjacent each other. The tunnel may extend through a first bone and a graft tissue. The bones may include at least a tibia, femur, glenoid or fibula. The tunnel may define a first opening and a second opening at the opposite end of the tunnel. The flexible member may be transported such that it extends from both the first and second openings, or alternatively is coupled to elements that extend from both openings. The system also includes a guide or instrument that includes an aperture or opening for receiving the flexible member therethrough after the flexible member exits the second opening. The aperture or opening cooperates with the flexible member and retains a portion of the flexible member within the guide opening. The guide includes a handle configured to draw the flexible member portion away from the second opening. The handle is configured so as to manipulate the guide through a skin incision that is laterally spaced from the tunnel second opening and preferably is an incision that is formed for other portions of the procedure.

In some embodiments the retained flexible member portion has an expandable element operatively coupled thereto. The transporting means may dispose the expandable element through the guide aperture. The expandable element changes shape from a first cross sectional configuration that fits through the aperture, to a second cross sectional configuration that does not fit through the aperture and thereby captures the flexible member portion at the second opening and with the guide aperture. This inhibits the flexible member from retracting back into the tunnel. The expandable element may be selected from a group consisting of an all-suture anchor; a rigid anchor; a toggle or a cortical button. In some example embodiments the transportation means may include an outer tube and an inner tube, both sized to fit through the guide aperture. The outer tube may house the expandable element while in the first cross sectional configuration and the inner tube may cooperate with the flexible member to change the expandable element to the second cross sectional configuration. In some example embodiments the transporting means may include an outer tube and an inner rod, the outer tube configured to house the expandable element while in the first cross sectional configuration and wherein the inner rod is configured to cooperate with the flexible member to change the expandable element to the second cross sectional configuration. In some embodiments the guide aperture defines a portion of a drill guide. The guide may draw the flexible portion laterally away from the second opening and may draw the flexible portion through an incision formed also to place the drill guide and drill the tunnel. In some example embodiments the guide aperture may be defined by a suture capture member having at least one flexible arm. The at least one flexible arm may define a first surface of the aperture and wherein the transporting means may causes the flexible arm to flex and allow passage of the flexible member therethrough. The flexible arm may then spring back to capture the flexible member within the guide aperture. In some example embodiments the suture capture member is a cartridge configured to selectively couple to a drill guide.

Also disclosed herein is an example method of managing a flexible shuttle member along a tunnel including placing a drill guide around at least one bone, the at least one bone have a prepared tunnel therethrough defining a first and second tunnel opening. An aperture of the drill guide is placed adjacent the second tunnel opening formed through the at least one bone. A flexible shuttle member is then inserted through the tunnel, and through the drill guide aperture. A first end of the flexible shuttle member is then captured by the drill guide aperture. The drill guide and flexible shuttle member first end is withdrawn away from the tunnel, while a second end of the flexible shuttle member extends from the tunnel first opening, such that the flexible shuttle member extends from both the first and second tunnel openings. A secondary element is then coupled to the first end of the flexible shuttle member and the second end of flexible shuttle member withdrawn to draw at least a portion of the secondary element into the tunnel second opening.

In some embodiments the method may include deploying an expandable element operably coupled to the flexible shuttle member first end to capture the first end of the flexible member with the drill guide aperture. The method may include deflecting a spring arm associated with the drill guide aperture to capture the first end of the flexible shuttle member with the drill guide aperture. The method may include drilling the tunnel using a drill that extends along a cannulation of the drill guide and then, removing the drill and maintaining the position of the drill guide. The flexible shuttle member may then be inserted through the tunnel using an instrument that may also extends along the guide cannulation. The method may include withdrawing the drill guide and thereby the flexible member first end laterally away from the tunnel and through a skin incision formed to place the drill guide adjacent or around the bone. The method may include disconnecting the flexible shuttle member first end from the drill guide once withdrawn from the tunnel and then coupling the secondary element thereto. The method may include removing the expandable member from the flexible member first end before coupling the secondary element to the flexible member.

A further example embodiment is disclosed of a suture transport system for placing a shuttling flexible member along a bone tunnel, the system including a flexible member and a flexible member insertion instrument. The insertion instrument inserts the flexible member into a first end of the bone tunnel through the bone tunnel and out of a second end of the bone tunnel. The system also includes a guide including an aperture for receiving the flexible member therethrough at the tunnel second end. The guide aperture and flexible member cooperate to capture the flexible member within the aperture and thereby at the tunnel second end. The guide may include a handle configured to withdraw the flexible member laterally away from the tunnel second end. The flexible member may include an expandable element operatively coupled thereto. The expandable element may be selected from a group consisting of and all-suture anchor; a rigid anchor; a toggle or a cortical button. The expandable element changes shape from a first cross sectional configuration that fits through the aperture, to a second cross sectional configuration that does not fit through the aperture and thereby captures the flexible member at the second opening. The aperture may also receive a drill therethrough, while forming the tunnel. In some embodiments the guide aperture is at least partially defined by a suture capture member having at least one flexible arm. The at least one flexible arm defines a first surface of the aperture and wherein the insertion instrument includes a rod that flexes the flexible arm to place the flexible member through the aperture. The flexible arm may then spring back once the rod has been withdrawn and thereby capture the flexible member.

A further example embodiment of a system for transporting a shuttle suture is disclosed herein, the system including a drill guide having an aperture and a flexible member defining a first end and a second end, the second end having an expandable element operable coupled thereto. The flexible member, expandable element and drill guide aperture include a first elongate configuration wherein the flexible member and expandable element may extend through the drill guide distal opening. The flexible member, expandable element and drill guide aperture include a second captured configuration. In this second captured configuration the expandable element forms a cluster against a distal surface of the drill guide distal opening, the cluster configured to inhibit retraction of the expandable element and thereby the flexible member distal end through the drill guide distal opening.

NOTATION AND NOMENCLATURE

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

A flexible member may be defined to include a length of suture, a length of tape, or flexible wire.

An expandable element may include an element, separately formed from the flexible member, and is defined to include an element that may selectively laterally expand to form a larger cross section. Examples of expandable elements are described herein, and may include at least an all-suture anchor, a cortical button or a toggle anchor or key.

BRIEF DESCRIPTION OF THE DRAWINGS

For a detailed description of example embodiments, reference will now be made to the accompanying drawings in which.

DETAILED DESCRIPTION

The following discussion is directed to various embodiments. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The disclosure may generally include a method and system for transporting a flexible member such as a suture or tape from a first side of tissue to an opposite side of the tissue so as to be reliably discovered and manipulated thereafter. The method may include transporting the suture using a suture transporter assembly that may cooperate with a drill guide to reliably target the suture transport system through the tissue, maintain the flexible member within the tissue once transported and also allows for easy suture discovery at the opposing side. For example when used during ACL repair, the system may interact and be anchored with the ACL joint drill guide system.

Figure 1A:
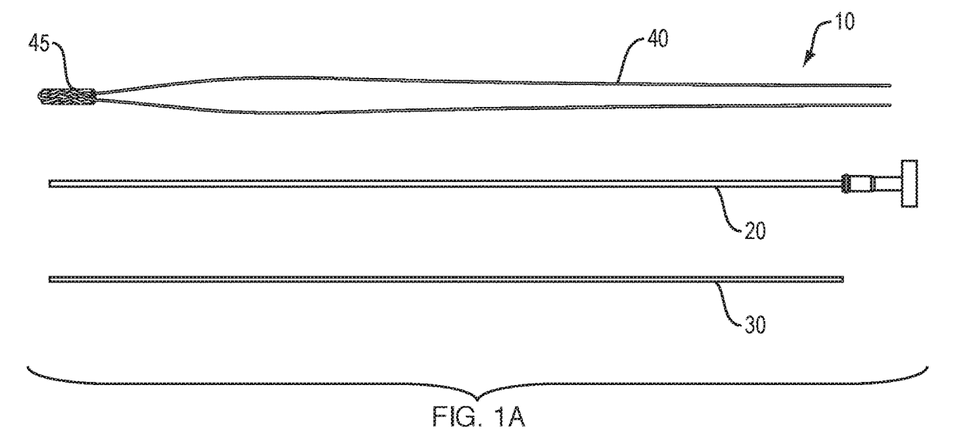
FIG. 1A illustrates unassembled components of a suture transporter assembly, in accordance with at least one embodiment disclosed.
Figure 1B:
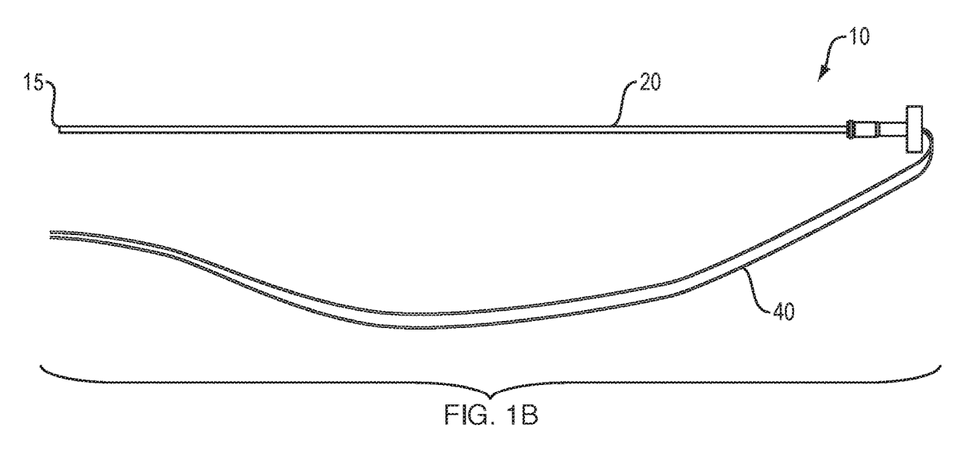
FIG. 1B illustrates an assembled suture transporter assembly, in accordance with at least one embodiment disclosed.

Referring now to FIGS. 1A and 1B, an exemplary embodiment of a flexible member transporter assembly 10 is illustrated in a disassembled arrangement, including an outer tube 20, an inner push tube 30 and flexible member 40. Flexible member 40 may be operatively coupled to an expandable element 45 as defined herein. Expandable element 45 is operable to have a first configuration that is shaped or oriented to nest within a distal end of outer tube 20 and upon ejection from outer tube 20 (possibly using push tube 30) may change orientation or change shape to have a larger cross section and thereby prevent retraction of element 45 and thereby flexible member 40 back into the tissue. One non-limiting example element may include a button style anchor that may be oriented in a first orientation while within the outer tube 20 and may rotate to a second orientation once out of outer tube 30. Other non-limiting examples may include all-suture anchors, disclosed in more detail in FIGS. 2A-2C and 3A-3C. The expandable element 45 provides a temporary means of maintaining the flexible member 40 at the opposite end of the tissue and therefore does not need to provide long-term fixation. Flexible member 40 may be a single flexible member, or may be a bight, forming a flexible member distal end and expandable element 45 disposed at the flexible member distal end.

Figure 2A:
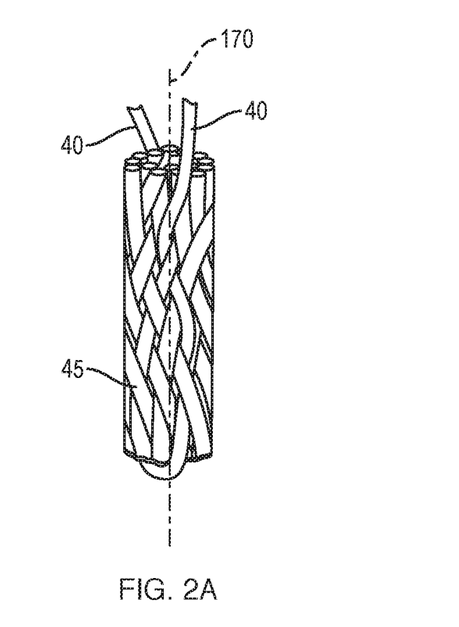
FIGS. 2A-2C illustrates an example embodiment and method of deployment of a flexible expandable element, in accordance with at least one embodiment disclosed.
Figure 2B:
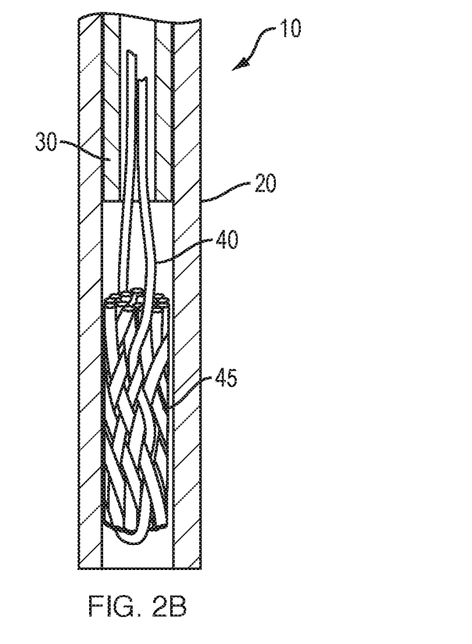
Figure 2C:
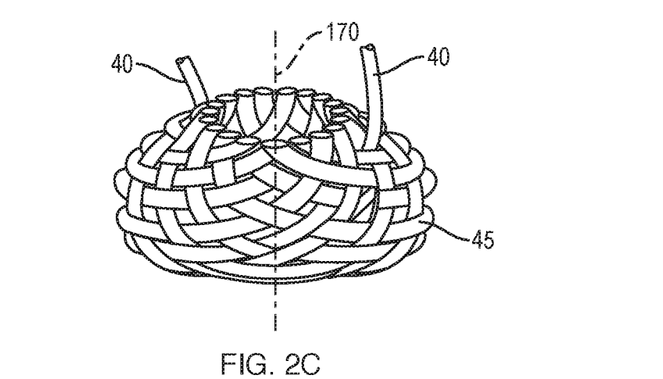

FIG. 1B shows the flexible member transporter assembly 10 with the outer tube 20 visible, the inner push tube 30 inserted therein. More detail of this assembly is shown in FIG. 2A-2C. The flexible member 40 may extend along the inner tube 30, with the expandable element 45 at a distal end of assembly, which as shown may be housed within outer tube 20. Example assembly 10 is described in more detail in U.S. Pat. No. 9,962,149, and incorporated in its entirety by reference herein. FIGS. 2A-2C show an example distal end of tube 20, tube 30 and flexible member 40. The embodiment of expandable element 45 shown in FIG. 2A is formed from a coarse braided material. More specifically, the structure utilized is a cylindrical, helically wound braid, such as the common biaxial braid. Pulling the entire braid along its length (i.e., putting the braid in tension) lengthens and narrows it. The length is gained by reducing the angle between the braided threads of the wound braid at the crossing points of the threads so that the braided threads align mostly parallel, which also reduces the radial distance between opposing sides and hence the overall circumference. When counter traction occurs, the opposite action occurs, and the braid contracts axially and expands radially, in this case by increasing the angle between the braided threads. This helically wound braid provides an advantage in that the structure can collapse and elongate naturally due to the alignment of the braids.

FIG. 2B shows the expandable element 45 in its elongated, compressed state and loaded into an inserter tube 20 in preparation for insertion through tissue and eventual deployment. The easily collapsible structure of the helically wound braid permits an installer to quickly and efficiently stretch the implant to the elongate position, and insert it into the inserter tube 20. Upon insertion into and through tissue to an opposite side of the tissue, deployment of the soft anchoring expandable element 45 by tensioning the flexible member 40, the fibers of the textile assume an orientation more orthogonally aligned with respect to the axis 170. FIG. 2C shows this deployed state, wherein the expandable element 45 is generally shortened and larger in diameter or cross section than in the pre-deployed state (FIG. 2A). In this example embodiment the outer tube may withdraw while the inner push tube 30 may remain stationary and tension on flexible member ends may deploy the expandable 45.

Figure 3A:
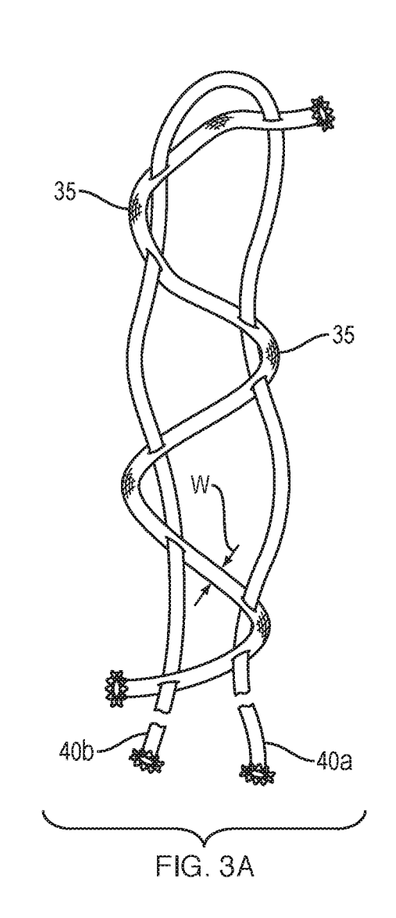
FIGS. 3A-3C shows an example embodiment and method of deployment of a flexible expandable element, in accordance with at least one embodiment disclosed.
Figure 3B:
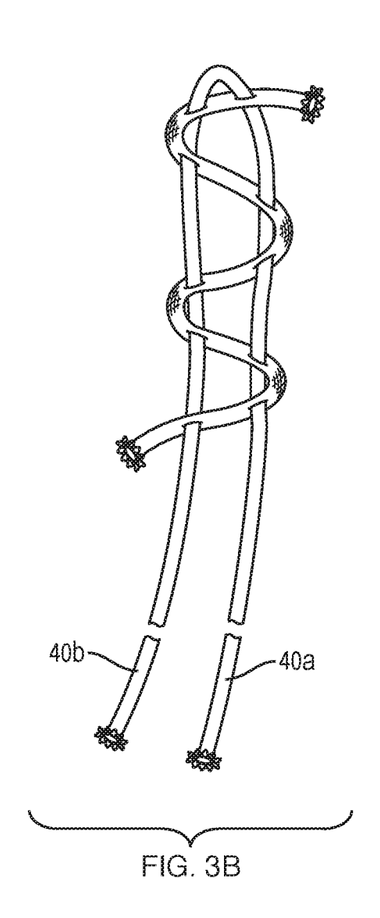
Figure 3C:
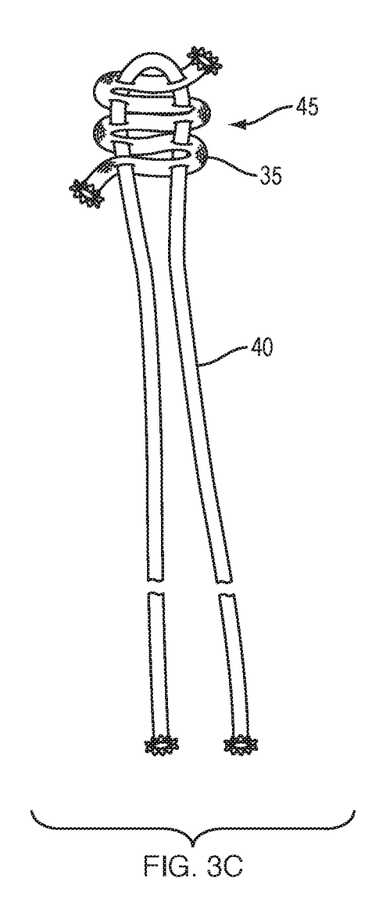

A second non-limiting example assembly is shown in FIGS. 3A-3C, similar to the assembly described in U.S. Pat. No. 8,795,334, incorporated in its entirety by reference herein. Expandable element 45 and a flexible member or flexible member 40 is interwoven through the expandable element 45. The expandable element 45 may be formed of a malleable or flexible braided body, the body defining a plurality of openings formed crosswise through, or substantially along, the width W of the body. The flexible member 40 includes two terminal ends, 40a and 40b. One of the terminal ends 40a, 40b is passed through each of the openings in the body forming multiple curved portions 35 of the fixation member 45 to form substantially S-shaped curved portions 35. The curved portions 35 may slide with respect to the flexible member 40 to form a cluster or bunch including a number of folds as shown in FIG. 3C and at least two S-shaped curved portions is preferred. The cluster in conjunction with the terminal ends 40a, 40b, may be used to secure flexible member 40 transported through to an opposing side of tissue as will be described in more detail heretoforth. Expandable element 45 may be a tape, mesh, tube, or other type of malleable or flexible structure, and the flexible member 40 may be made from a flexible member of different size depending upon the surgical procedure or application. In an alternative assembly, push tube may be a rod or sliding member operably coupled to expandable element 45. The user may advance the rod 30 forward within the outer tube 20 to deploy the expandable element 45 from the outer tube 20.

Figure 4A:
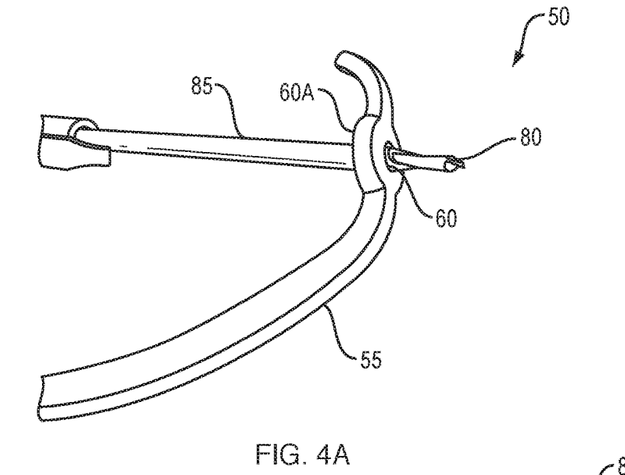
FIGS. 4A-4C show a method of transporting and capturing a flexible member using a drill guide, in accordance with least one embodiment disclosed.
Figure 4B:
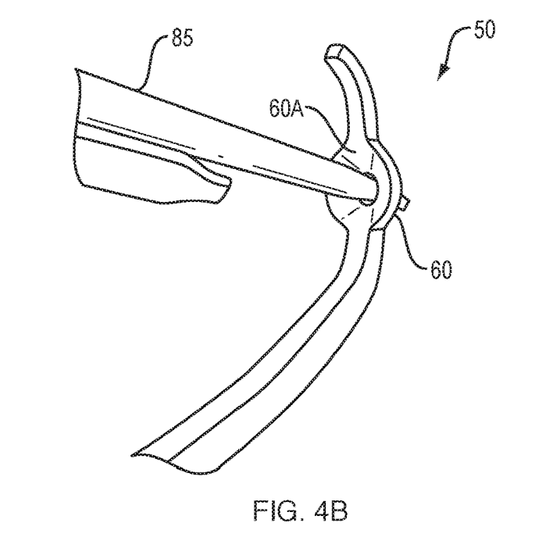
Figure 4C:
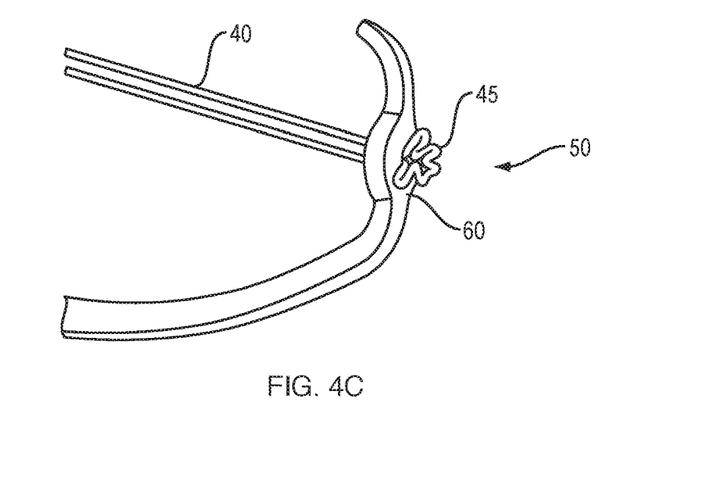

Assembly 10 may cooperate with a drill guide 50, illustrated in FIGS. 4A-4C. Drill guide 50 may be similar to known ACL drill guides and may include an aperture 60 sized for receiving a drill tip 80 therethrough. Drill tip 80 may slide within a drill guide cannula 85, and cannula 85 may define an OD that inhibits the cannula from extending through aperture 60, and therefore abuts a first side 60A of aperture 60. Once drill tip 80 is removed from cannula 85, assembly 10 may then be inserted along cannula 85 and through aperture 60. Assembly outer tube 20 is therefore sized to extend through drill cannula 85 and aperture 60. Expandable element 45 may then be deployed so as have a second larger cross sectional shape or orientation, preventing expandable element 45 and thereby flexible member 40 from extending back through aperture 60, as shown in FIG. 4C. FIG. 4C shows the expandable element embodiment disclosed in FIG. 3A-3C. Expandable element 45 is disposed on the far side 60B of aperture 60. Drill guide 55 may then be removed, drawing the flexible member 40 and expandable element 45 with it. The flexible member 40 is sufficiently long or coupled to a further surgical device such that it remains disposed along the tunnel and out of both openings of the tunnel for later shuttling. The captured portion of the flexible member may then be disengaged from the drill guide and a secondary element such as tissue or surgical device may be selectively coupled to flexible member 40. Pulling the opposite end of flexible member 40 may then draw or shuttle the secondary element into the tissue tunnel.

Figure 5A:
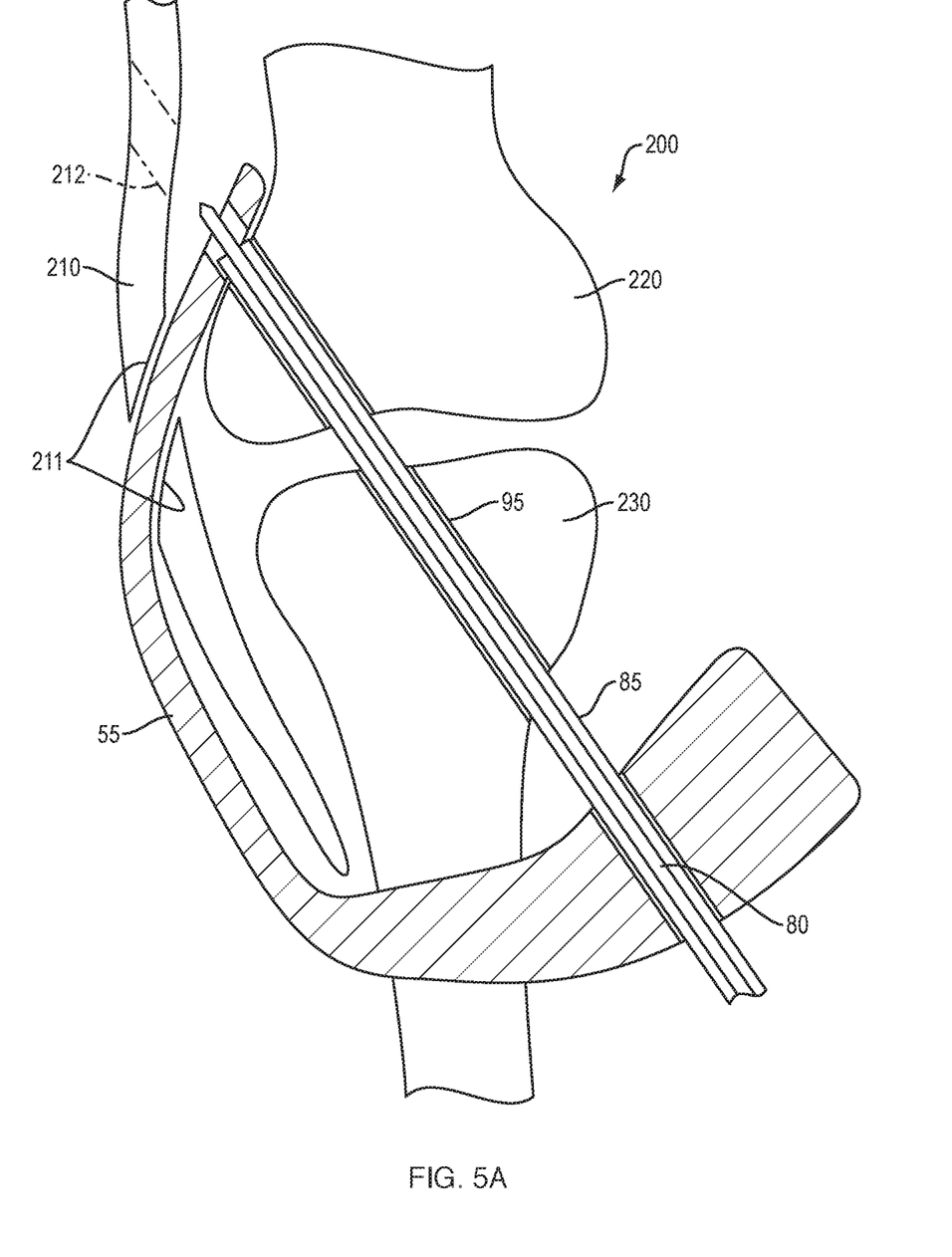
FIGS. 5A-5D show a method of transporting and capturing a flexible member through an ACL tunnel using a drill guide, in accordance with least one embodiment disclosed.
Figure 5B:
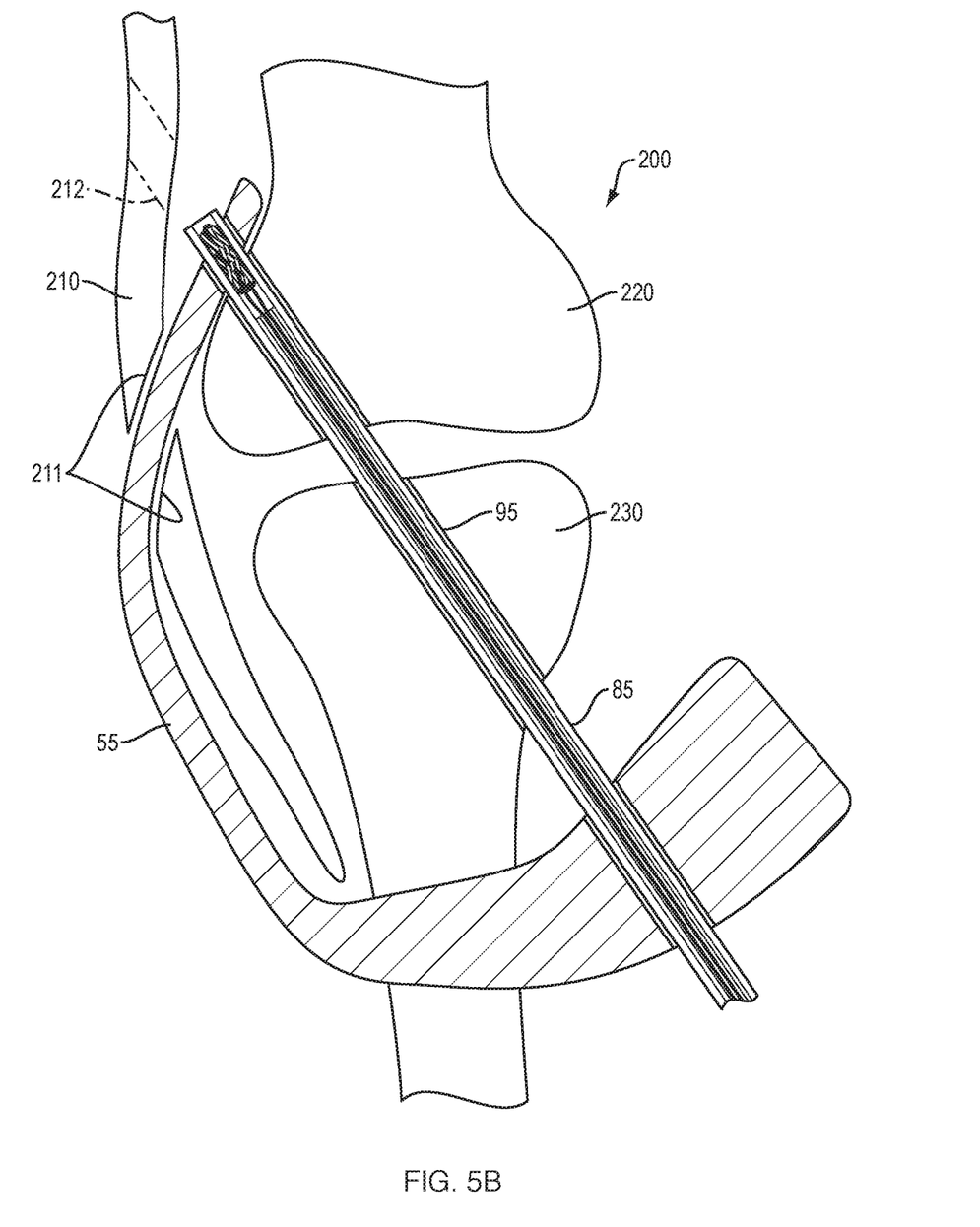
Figure 5C:
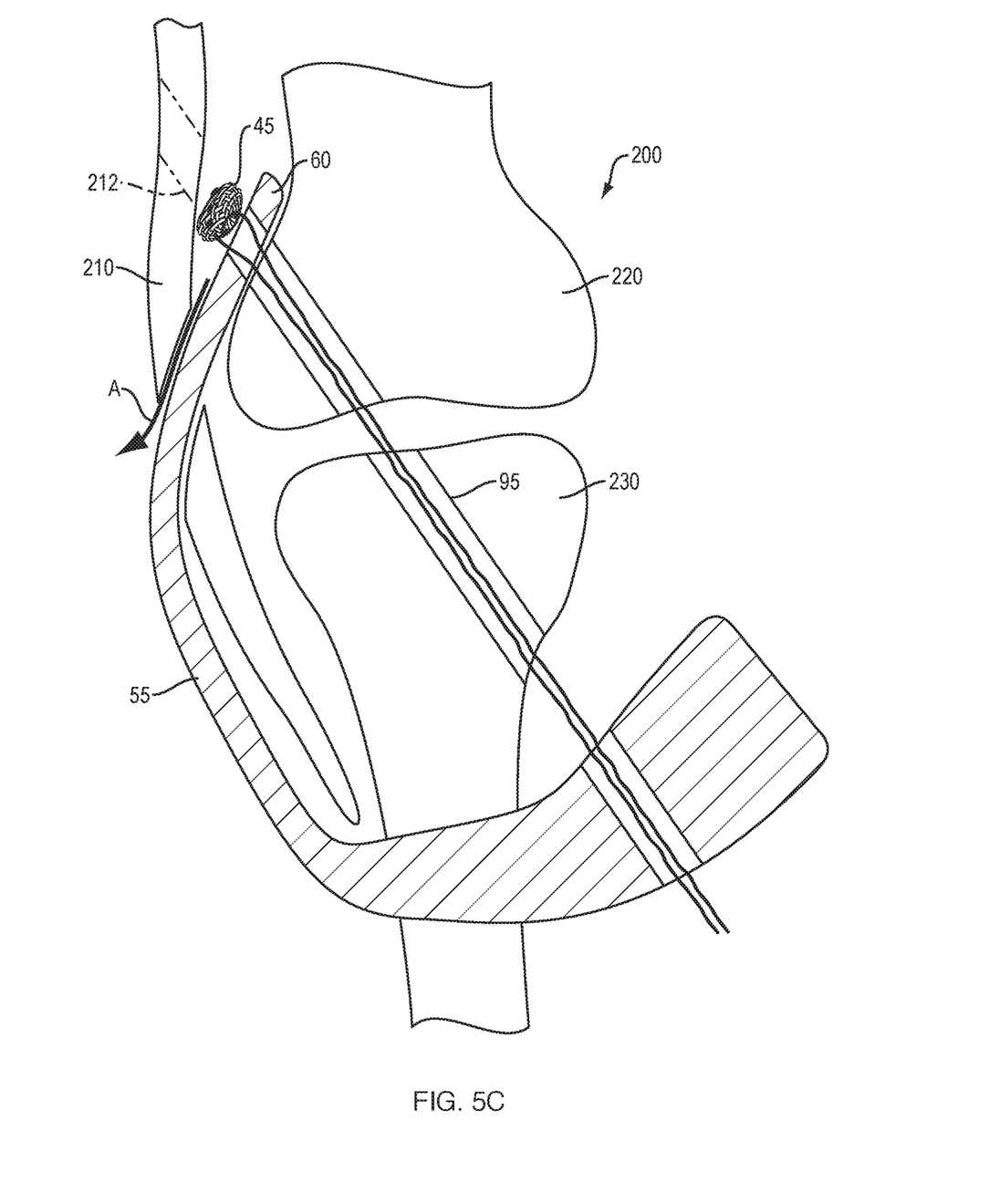
Figure 5D:
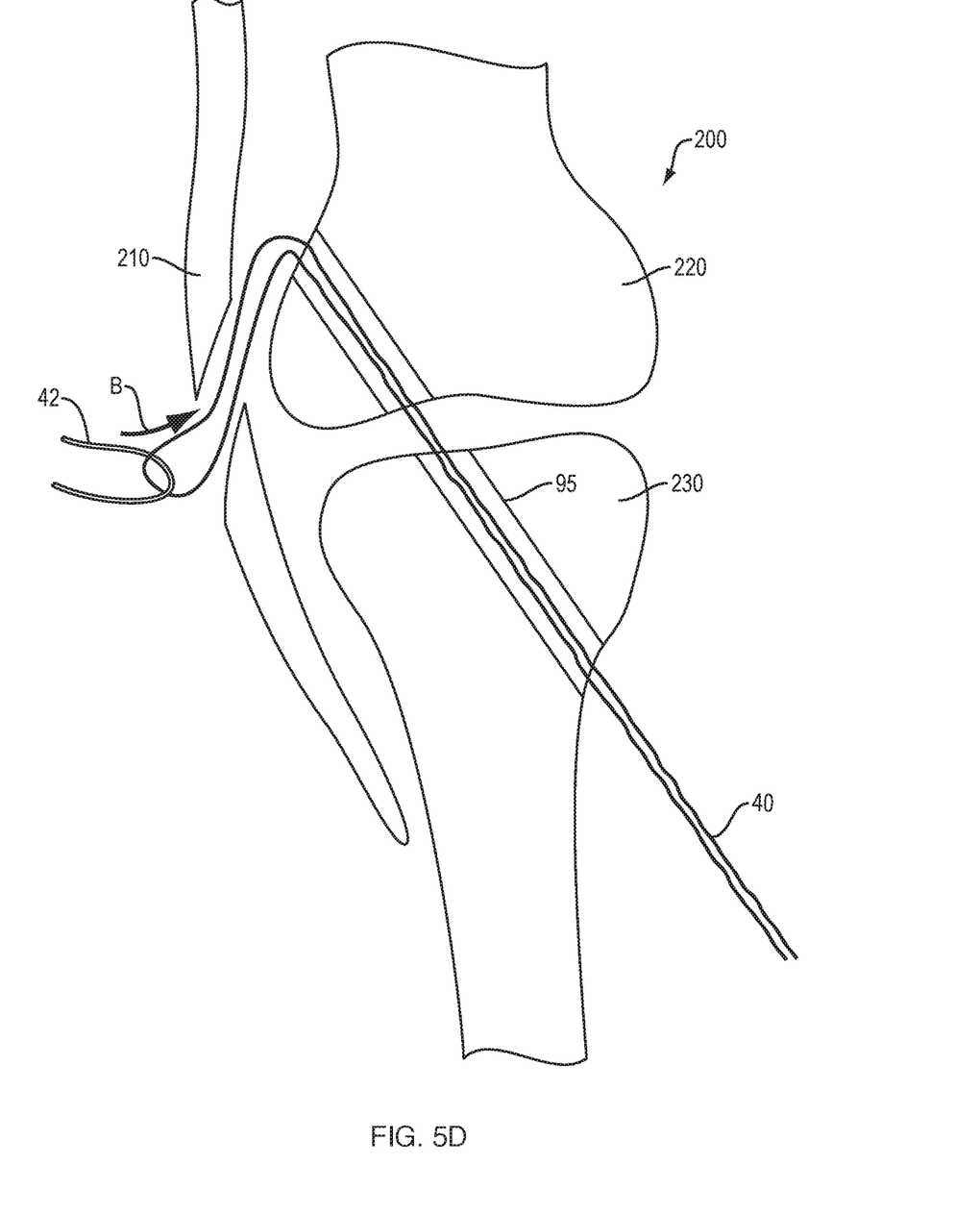

An example method of transporting and capturing a flexible member 40 that may be used to shuttle a secondary device during a surgery of the knee 200 is shown in FIGS. 5A-5D. FIG. 5A shows a femur 220, tibia 230 and a portion of the patient skin 210. Drill guide 55 is shown extending through a skin incision 211. In this procedure a second skin incision 212 is not needed. The method may include using the drill guide 55 to form a tunnel 95 through the bone. The tunnel 95 may have been prepared using a drill 80 that extends through a cannula 85, and the flexible member transporter assembly 10 may slide along the cannula 85 once the drill 80 has been removed. The method may include sliding a flexible member transporter assembly 10 through and along a prepared tunnel 95 and adjacent an aperture 60 of a drill guide. In some embodiments, an expandable element 45 is operatively coupled to the flexible member 40 and a distal portion of assembly 10 may be inserted through the aperture 60. The expandable element 45 may then be deployed to an expanded or deployed configuration that cooperates with the aperture 60 to prevent the expandable element 45 and flexible member 40 from being drawn back through the aperture 60 as shown in FIG. 5C. Drill guide and captured portion of flexible member 40 may then be removed from tunnel opening in the direction indicated by arrow A and through an existing skin incision formed to insert the drill guide 55. A second incision for example area around 212 is therefore avoided. The captured portion may be disengaged from the gill guide and coupled to a secondary element 42. Expandable element 45 may be removed to couple the secondary element 42. Secondary element 42 may be drawn into the tunnel, indicated by arrow B and shown in FIG. 5D.

Figure 7A:
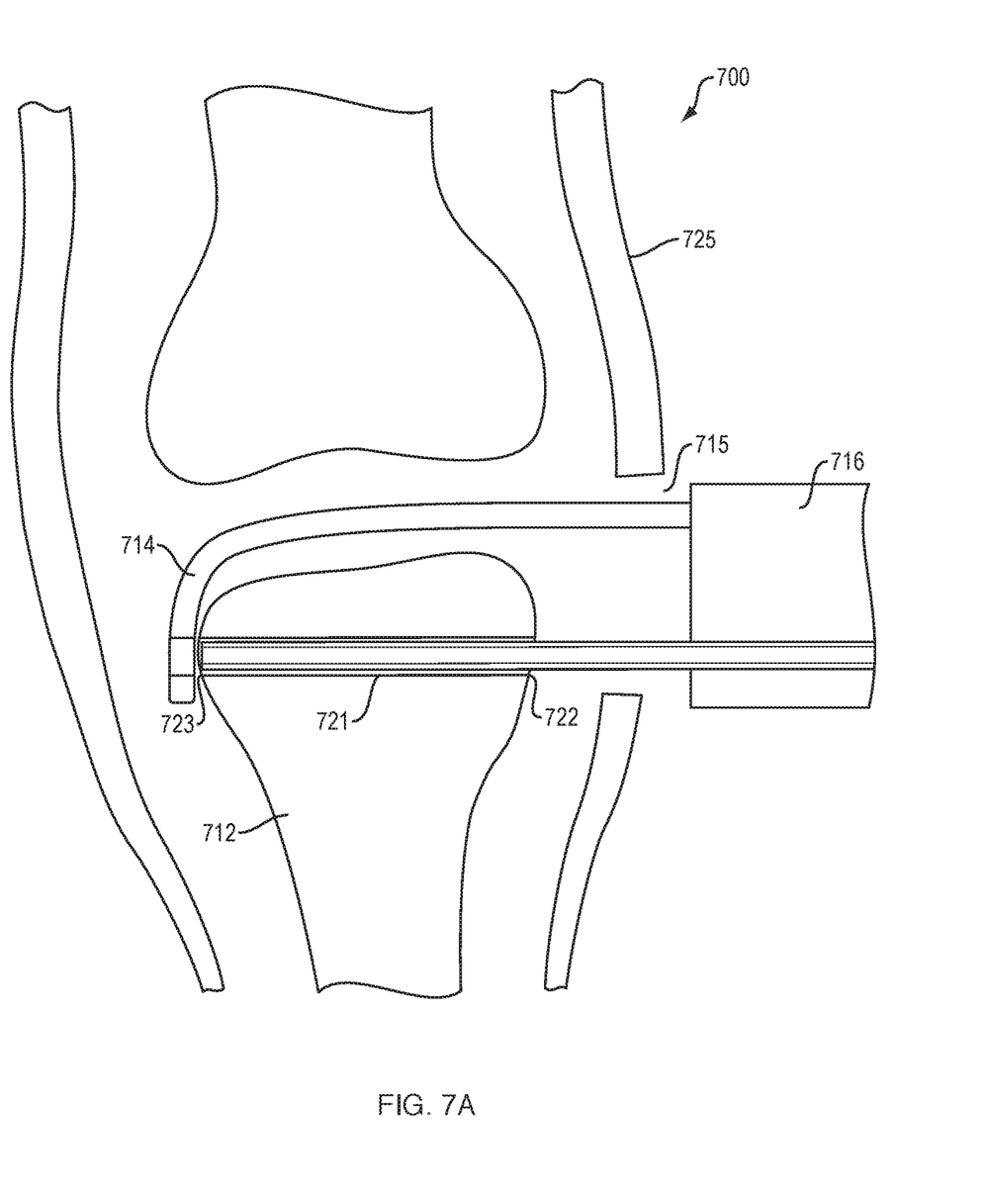
FIGS. 7A-7C illustrate a method of transporting and capturing a flexible member through a glenoid using a drill guide, in accordance with least one embodiment disclosed.
Figure 7B:
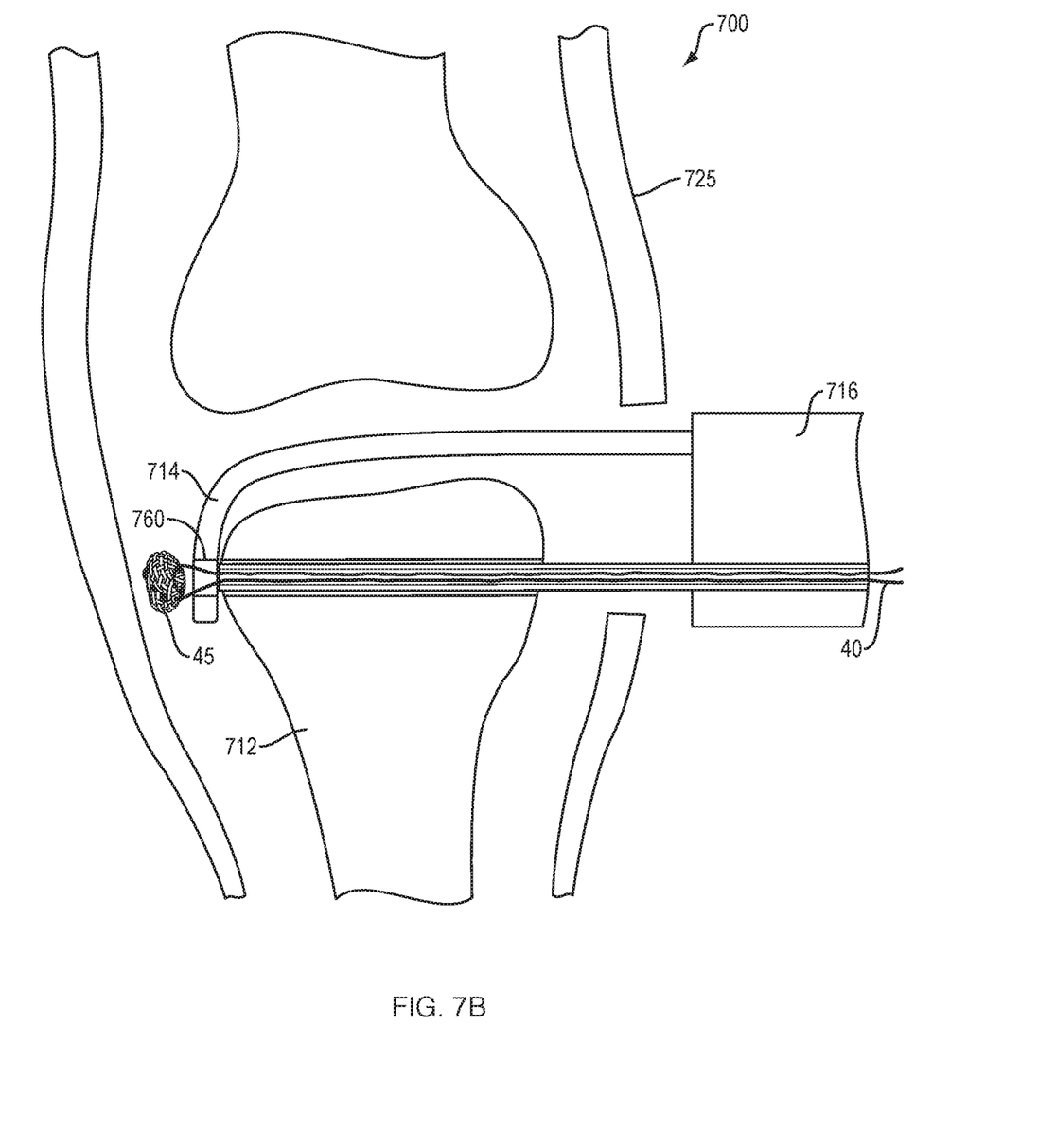
Figure 7C:
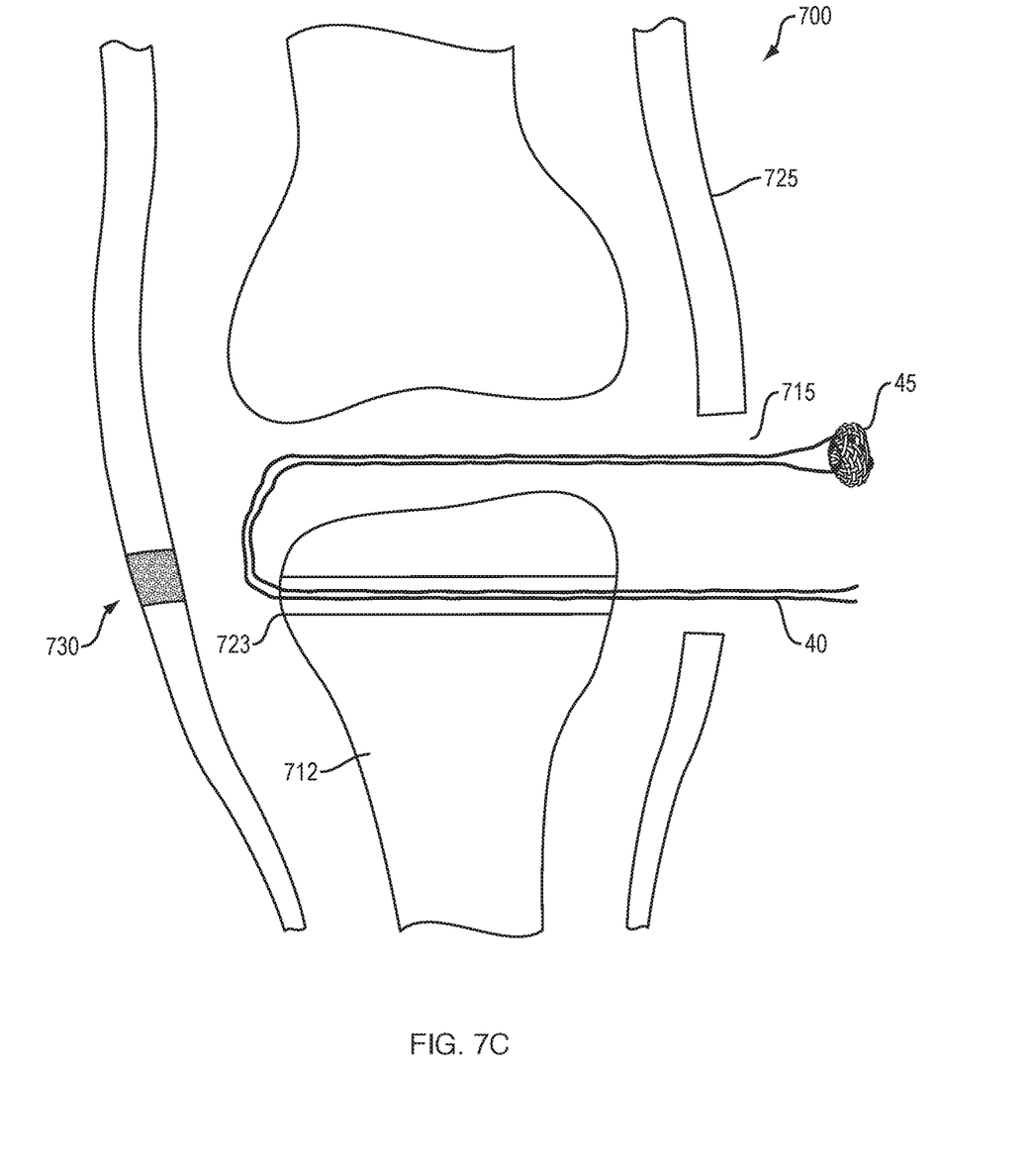

A further example method of transporting and capturing a flexible member 40 that may be used to draw a secondary element towards a tissue surface during surgery on the shoulder 700 is shown in FIGS. 7A-7C. Details of an example shoulder procedure that this method and system may be useful for, are disclosed in more detail in at least U.S. Pat. No. 9,402,650, commonly owned and herein incorporated in its entirety by reference. FIG. 7A shows a glenoid drill guide 716 inserted through a portal 715 in the patient's skin 725 adjacent the glenoid 712. An engagement member 714 on the distal end of the glenoid drill guide 716 (e.g., a hook) is placed at a selected position on the glenoid 710 and the drill guide 716 is aligned. Engagement member 714 may include a means to engage a suture transport system such as an aperture 760 as disclosed herein. A tunnel 721 is shown drilled from a first glenoid surface 722 to a second surface 723 and the second surface may be configured to receive a graft thereon. A drill bullet (not shown) may form a tunnel. The method may include using the drill guide 716 to form a tunnel 721 through the bone. Illustrated in FIG. 7B the flexible member transporter assembly 10 may then be inserted through tunnel 721, and may be inserted along a cannulation of the drill guide 716. In some embodiments, an expandable element 45 is operatively coupled to the flexible member 40 and a distal portion of assembly 10 may be inserted through the aperture 760. The expandable element 45 may then be deployed to an expanded or deployed configuration that cooperates with the aperture 760 to prevent the expandable element 45 and flexible member 40 from being drawn back through the aperture 760 as shown in FIG. 7B. Engagement member 714 and captured portion of flexible member 40 may then be removed through portal 715, illustrated in FIG. 7C. The captured portion may be disengaged from the engagement member 714 (and drill guide) and coupled to a secondary element (not shown). Expandable element 45 may be removed to couple the secondary element. Secondary element may be drawn through portal 715, around the glenoid and may be drawn towards the second surface 723. Secondary element may be drawn into the tunnel 721. A second incision for example area around area 730 is therefore avoided to place a secondary element adjacent second surface 723. Secondary element may be a coracoid graft that may be attached to the second surface 723 of the glenoid 712. The method may therefore include coupling a coracoid graft (not shown) to the flexible member 40 and drawing the coracoid graft onto the surface 723.

Figure 6A:
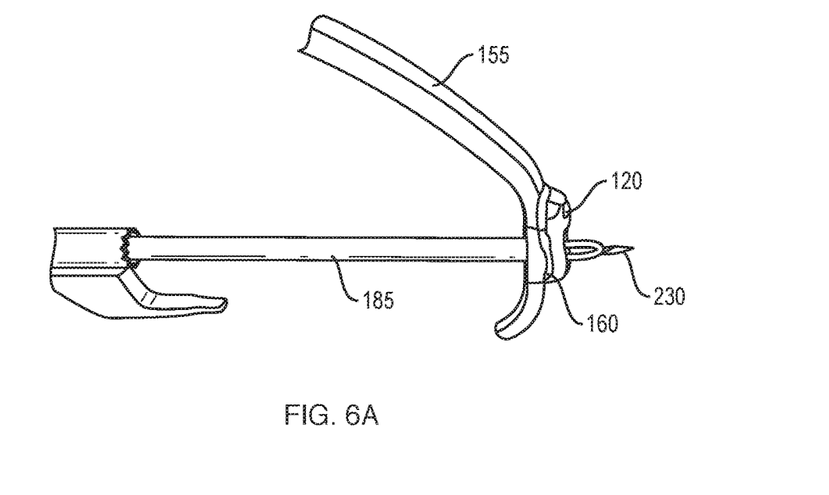
FIGS. 6A-6C show an alternative embodiment of a flexible member transport and capture assembly using a suture capture member, in accordance with the disclosure.
Figure 6B:
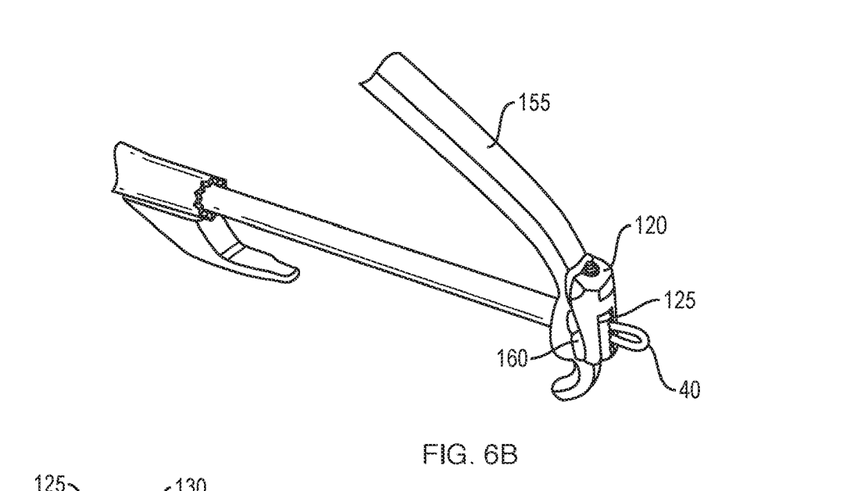
Figure 6C:
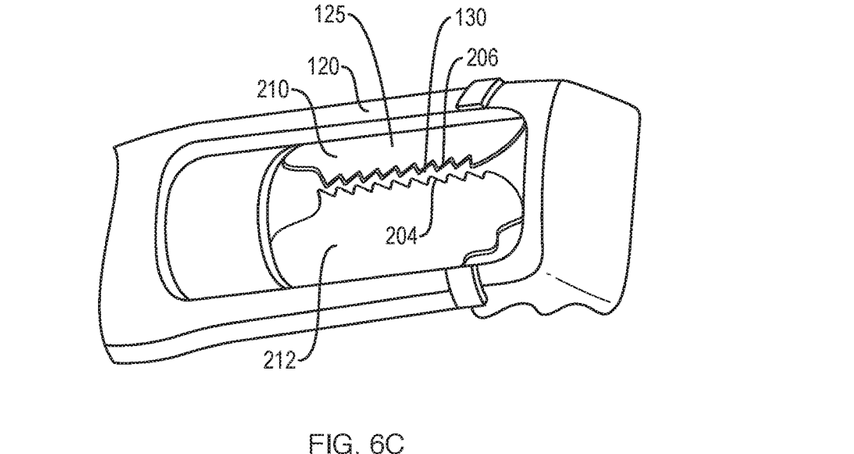

An alternative embodiment of a suture transporter system may include a flexible suture member capture member(s) 120 associated with the drill guide 155, schematically shown in FIGS. 6A-6C. This may eliminate the need for an expandable element as described in previous embodiments. Flexible member 40 may therefore be pushed through cannula 185 by a forked rod for example, which pushes the flexible member 40 through an aperture 160 of the drill guide and then through an aperture of the flexible capture member 120. Suture capture member 120 may, in some embodiments comprise a suture capture cartridge selectively disposed over aperture 160, aperture 160 being configured to receive a drill tip 80 as disclosed in previous embodiments. Suture capture cartridge may selectively couple and uncouple from drill guide 155. Alternatively, suture capture member 120 may be a separate instrument having a handle that may place suture capture member 120 adjacent drill guide aperture 160. Referring now to FIGS. 6A, 6B and 6C, suture capture member 120 comprises an elongate aperture 130 formed by edges 204, 206 on each opposed side. Edges 204, 206 may further comprise suture capture surfaces 208 in certain embodiments. Suture capture member may operate in a similar manner to the suture cartridge disclosed in more detail in U.S. Pat. No. 9,211,118, commonly owned and herein incorporated in its entirety by reference. Suture capture surface 208 may be configured as opposed serrated edges, a plurality of interdigitating teeth, a plurality of opposed notches, or other similar opposed edge features. Suture capture cartridge 125 further comprises deflecting portions 210, 212 (i.e., arms 210, 212) which extend from edges 204, 206 respectively, and may be formed in a curved or arcuate shape. In certain embodiments, cartridge 125 and/or the components of suture capture member 120 are preferably comprised of high temper spring steel material.

The flexible member 40 may therefore by pushed through cannula 185, with a forked push rod 230, the forked portion configured to hold a flexible member 40. Forked push rod 230 is advanced through aperture 130 and thereby between deflecting portions 210, 212. As forked rod and flexible member 40 pass through aperture 130, forked rod 230 contacts edges 204, 206 such that each of arms 210, 212 are deflected away from rod 230. The deflection of arms 210, 212 is designed to be elastic such that arms 210, 212 respectively return to or spring back into a pre-deflected or lesser-deflected position upon the subsequent withdrawal of rod 130 through aperture 130. With the flexible member bight portion 40' protruding through suture capture member 120, rod 230 may be withdrawn through aperture 130 and returned to a retracted position. As rod 230 is withdrawn through suture capture member 120, arms 210, 212 spring back to a non-deflected position such that aperture 130 and suture capture surface 208 are allowed to close around flexible member bight portion 40'. Aperture 130 is large enough and the spring deflection of arms 210, 212 is great enough that these characteristics of suture capture member 120 do not restrict the movement of rod 230 during displacement to the extended position. In addition, aperture 130 is sufficiently small when arms 210, 212 are in the non-deflected configuration so that flexible member portion 40' is not allowed to pass back through suture capture member 120. A loop or bight of flexible member 40' then remains between edges of suture capture member 125. Drill guide 155 or just the removable cartridge 125 may then be removed from tunnel end, drawing the bight portion 40' with it. While drawing the bight portion 40' away from the tunnel end, the flexible member 40 may be sufficiently long to extend from both end of the tunnel. Flexible member bight portion 40' may then be disengaged from cartridge 125. A secondary element such as tissue or surgical device may be selectively coupled to bight portion 40' as described previously. Flexible member 40 may therefore act as a shuttling member.

The method of transporting and capturing the flexible member 40 may therefore include preparing a tunnel through tissue, which may include using a drill guide having a distal opening for guiding the second or distal end of the tunnel location. A suture capture member may then be placed near the second end of the tunnel and may be operatively coupled to the drill guide and over the distal opening of the drill guide. A suture transporter push rod 230 selectively coupled to a flexible member 40 may then be inserted from a tunnel first or proximal end through the prepared tunnel 95 and through an aperture 160 of a drill guide. Drill guide may include a cannula 185 and the tunnel 95 may have been prepared using a drill 80 that extends through cannula 185; the push rod 230 may also slide along the cannula 85 once the drill 80 has been removed. Suture capture member 120 may include at least one flexible arm member defining a portion of a suture capture slot or aperture 130. Push rod 230 may be operable to elastically deflect flexible arm member to place a bight portion 40' of flexible member 40 through aperture 130 and upon withdrawal of push rod 230 from within the aperture, the flexible member 40 may be released from push rod 230 and captured by the aperture 130 as the flexible arm springs back. Suture capture member 120 may then be removed, with a portion 40' of the flexible member 40 captured therein, the flexible member 40 still extending from the first or proximal opening of tissue tunnel. The captured portion of the flexible member 40' may then be disengaged from the suture capture member 120 and may be coupled to a second element such as but not limited to a second suture, flexible member, medical device or tissue such as a graft. Tension on the flexible member extending from the proximal tunnel opening may draw the second element towards the tunnel. Tension may further draw the second element into the tunnel second end.

Numerous variations and modifications will become apparent to those skilled in the art once the above disclosure is fully appreciated. It is intended that the following claims be interpreted to embrace all such variations and modifications.

The invention claimed is:

1. A shuttle system comprising:
a means of transporting a flexible member along a tunnel through a tissue from a first opening of the tunnel through to a second opening at an opposite end of the tunnel, such that the flexible member extends from both the first and second openings;
a guide having an aperture for receiving the flexible member therethrough after exiting the second opening, the aperture configured to cooperate with the flexible member and capture a portion of the flexible member at the second opening and wherein the guide includes a handle configured to draw the flexible member portion, once captured, around the tissue, away from the second opening and towards the first opening, wherein the guide aperture includes at least one flexible arm configured to flex and allow passage of the flexible member through the guide aperture and capture the flexible member.

2. The shuttle system of claim 1 wherein the guide is a drill guide, configured to guide a drill during formation of the tunnel.

3. The shuttle system of claim 1 wherein the at least one flexible arm is configured to selectively assemble to the guide.

4. A suture transport system for placing a shuttling flexible member along a bone tunnel, the system comprising:
a flexible member;
a flexible member insertion instrument configured to insert the flexible member into a first end of the bone tunnel through the bone tunnel and out of a second end of the bone tunnel; and
a guide including an aperture for receiving the insertion instrument and flexible member therethrough at the tunnel second end and configured to capture the flexible member within the aperture, wherein the guide aperture includes at least one flexible arm, and wherein the flexible member insertion instrument is configured to flex the at least one flexible arm to place a portion of the flexible member through the aperture.

5. The suture transport system of claim 4 wherein the guide includes a handle configured to withdraw the flexible member that is captured laterally away from the tunnel second end and through a portal adjacent the tunnel first end.

6. The suture transport system of claim 4, wherein the guide includes an arm that extends around the bone and is configured to guide a drill to form the bone tunnel.

7. The shuttle system of claim 1 wherein the means of transporting is configured to push the flexible member through the guide aperture and deflect the at one flexible arm.

8. The shuttle system of claim 7 wherein the at least one flexible arm defines a side of an elongate narrow aperture.

9. A suture transport system for coupling a surgical component to a target tissue, the system comprising:
a flexible member;
an insertion instrument having a handle end and a distal end, the distal end configured to engage the flexible member, the insertion instrument configured to insert the flexible member through the target tissue, from a first external surface of the target tissue to a second external surface of the target tissue; and
a capturing tool including an aperture and a handle, the aperture configured to be placed at the target tissue second external surface and receive the insertion instrument distal end therethrough, the aperture including a spring arm configured to be deflected by the insertion instrument distal end to receive the flexible member therethrough and then spring back upon retraction of the insertion instrument distal end, to capture the flexible member.

10. The suture transport system of claim 9 wherein the capturing tool extends around the target tissue and is configured to draw a portion of the flexible member captured within the aperture away around an external surface of the target tissue for coupling the surgical component to the flexible member.

11. The suture transport system of claim 9 wherein the spring arm is configured to be selectively removed from the capturing tool.

12. The suture transport system of claim 9 wherein the capture tool is a drill guide configured to direct a drill through the target tissue.

* * * * *